(12) United States Patent
Cheruku et al.

(10) Patent No.: US 11,053,203 B2
(45) Date of Patent: Jul. 6, 2021

(54) ONE-POT HOMOGENEOUS PROCESS FOR THE LARGE SCALE MANUFACTURE OF 2-SUBSTITUTED BENZIMIDAZOLES

(71) Applicant: Ecolab USA Inc., St. Paul, MN (US)

(72) Inventors: Pradeep Cheruku, Bolingbrook, IL (US); Suresh R. Sriram, Aurora, IL (US); James Joseph Michels, Naperville, IL (US)

(73) Assignee: ECOLAB USA INC., St. Paul, MN (US)

( * ) Notice: Subject to any disclaimer, the term of this patent is extended or adjusted under 35 U.S.C. 154(b) by 188 days.

(21) Appl. No.: 16/185,304

(22) Filed: Nov. 9, 2018

(65) Prior Publication Data
US 2019/0144395 A1    May 16, 2019

Related U.S. Application Data

(60) Provisional application No. 62/585,278, filed on Nov. 13, 2017.

(51) Int. Cl.
*C07D 235/12* (2006.01)
*C07D 235/18* (2006.01)
*C07D 235/08* (2006.01)
*C07D 401/04* (2006.01)
*C23F 11/14* (2006.01)

(52) U.S. Cl.
CPC ......... *C07D 235/12* (2013.01); *C07D 235/08* (2013.01); *C07D 235/18* (2013.01); *C07D 401/04* (2013.01); *C23F 11/149* (2013.01)

(58) Field of Classification Search
CPC .................................................. C07D 235/18
See application file for complete search history.

(56) References Cited

U.S. PATENT DOCUMENTS

| | | | |
|---|---|---|---|
| 3,784,517 A | 1/1974 | Hedberg et al. | |
| 4,001,268 A | 1/1977 | Kovar et al. | |
| 5,510,494 A | 4/1996 | Dietz et al. | |
| 6,124,470 A | 9/2000 | Angenendt et al. | |
| 7,608,722 B2 | 10/2009 | Heitger et al. | |
| 8,362,269 B2 | 1/2013 | Ehlenz et al. | |
| 2014/0066629 A1 | 3/2014 | Goldfinger et al. | |
| 2016/0348252 A1 | 12/2016 | Rane et al. | |
| 2017/0152245 A1 | 6/2017 | Huang et al. | |

FOREIGN PATENT DOCUMENTS

| | | |
|---|---|---|
| CA | 2471730 C | 7/2003 |
| CN | 101891689 A | 11/2010 |
| CN | 101979383 A | 2/2011 |
| CN | 102050791 A | 5/2011 |
| CN | 102250021 A | 11/2011 |
| CN | 102659686 A | 9/2012 |
| CN | 102827083 A | 12/2012 |
| CN | 103145623 A | 6/2013 |
| CN | 103435551 A | 12/2013 |
| CN | 103910682 A | 7/2014 |
| CN | 104974096 A | 10/2015 |
| CN | 105198819 A | 12/2015 |
| DE | 2900506 A1 | 7/1980 |
| EP | 0612732 A1 | 8/1994 |
| EP | 2886536 A1 | 6/2015 |
| GB | 943569 A | 12/1963 |
| IN | 201401729 I3 | 9/2014 |
| SU | 819098 A1 | 4/1981 |
| SU | 1164232 A1 | 6/1985 |
| WO | WO 2003/059890 A1 | 7/2003 |
| WO | WO 2006/034418 A2 | 3/2006 |
| WO | WO 2007/009967 A1 | 1/2007 |
| WO | WO 2009/116089 A2 | 9/2009 |
| WO | WO 2009/133122 A1 | 11/2009 |
| WO | WO 2012/028925 A2 | 3/2012 |
| WO | WO 2012/070068 A2 | 5/2012 |
| WO | WO 2013/189847 A1 | 12/2013 |
| WO | WO 2016/191672 A1 | 12/2016 |
| WO | WO 2017/100525 A1 | 6/2017 |

OTHER PUBLICATIONS

Mahesh et al. ("Copper(II)-Catalyzed Oxidative Cross-Coupling of Anilines, Primary Alkyl Amines, and Sodium Azide Using TBHP: A Route to 2-Substituted Benzimidazoles" J. Org. Chem., 2016, 81, 3227-3234) (Year: 2016).*

Azarifar, Davood et al., "Acetic acid-promoted condensation of o-phenylenediamine with aldehydes into 2-aryl-1-(arylmethyl)-1H-benzimidazoles under microwave irradiation," Journal of the Serbian Chemical Society (2010) 75(9): 1181-1189.

Chen, Jyh-Chien et al., "Novel polyimides containing benzimidazole for temperature proton exchange membrane fuel," Journal of Membrane Science (2015) 483: 144-154.

Cui, Wenge et al., "Efficient One-Pot Synthesis of 2-Substituted Benzimidazoles from Triacyloxyborane Intermediates," Synlett (2012) 23: 247-250.

Di, Suqing et al., "Enhancing the high-temperature proton conductivity of phosphoric acid doped poly(2,5-benzimidazole) by preblending boron phosphate nanoparticles to the raw materials," Journal of Power Sources (2012) 211: 161-168.

Dutta, Alokdut et al., "Correlating electronic structure with corrosion inhibition potentiality of some bis-benzimidazole derivatives for mild steel in hydrochloric acid: Combined experimental and theoretical studies," Corrosion Science (2015) 98: 541-550.

(Continued)

*Primary Examiner* — Peter F Godenschwager

(74) *Attorney, Agent, or Firm* — Eric D. Babych; Barnes & Thornburg LLP

(57) ABSTRACT

2-substituted benzimidazoles and methods of preparing the same are disclosed. The compositions may include a compound or salt thereof, an acid, and a polar aprotic solvent. The compositions may be used to inhibit corrosion of a metal surface in contact with an aqueous system, and provide enhanced protection against corrosion of metals in the aqueous system.

13 Claims, No Drawings

(56) References Cited

OTHER PUBLICATIONS

Getvoldsen, Gareth et al., "Microwave-assisted cyclocondensation of 1,2-diaminobenzene with [4-$^{18}$F]fluorobenzoic acid: microwave synthesis of 2-([4-$^{18}$F]fluorophenyl) benzimidazole," Journal of Labelled Compounds and Radiopharmaceuticals (2004) 47: 139-145.

Kaul, Savita et al., "Simple and Convenient One-Pot Synthesis of Benzimidazoles and Benzoxazoles using N,N-Dimethylchlorosulfitemethaniminium Chloride as Condensing Agent," Synthetic Communications (2007) 37: 2457-2460.

Katritzky, Alan R. et al., "A New Synthetic Method for the 2-Substitution of N-Unsubstituted Benzimidazoles: Formaldehyde as a Versatile Protecting Agent for Heterocyclic NH," Journal of Organic Chemistry (1989) 54(12): 2949-2952.

Kim, Hyoung-Juhn et al., "ABPBI Membrane for a Fuel Cell Application," Polymer Preprints (2004) 45(1): 933-934.

Krishnan, Palanichamy et al., "Performance of a poly(2,5-benzimidazole) membrane based high temperature PEM fuel cell in the presence of carbon monoxide," Journal of Power Sources (2006) 159: 817-823.

Lin, Shou-Yuan et al., "Microwave-assisted one step high-throughput synthesis of benzimidazoles," Tetrahedron Letters (2006) 47: 2883-2886.

Maras, Nenad et al., "Boric Acid-Catalyzed Direct Condensation of Carboxylic Acids with Benzene-1,2-diamine into Benzimidazoles," Helvetica Chimica Acta (2011) 94(10): 1860-1874.

Niknam, K. et al., "Synthesis of 2-Substituted Benzimidazoles and Bis-benzimidazoles by Microwave in the Presence of Alumina-Methanesulfonic Acid," Journal of the Iranian Chemical Society (2007) 4(4): 438-443.

Phillips, Montague Alexandra, "The Formation of 2-Substituted Benziminazoles," Journal of the Chemical Society (Jan. 1, 1928) 0: 2393-2399.

Ueda, Mitsuru et al., "Poly(benzimidazole) Synthesis by Direct Reaction of Methoxyphthalic Acids and Tetramine," Journal of Polymer Science: Part A: Polymer Chemistry (1989) 27: 2815-2818.

Ueda, Mitsuru et al., "Poly(benzimidazole) Synthesis by Direct Reaction of Diacids and Tetramine," Macromolecules (1985) 18: 2723-2726.

Wang, Ying et al., "A simple and efficient one step synthesis of benzoxazoles and benzimidazoles from carboxylic acids," Tetrahedron Letters (2006) 47(28): 4823-4826.

Zhang, Fan et al., "Performance and theoretical study on corrosion inhibition of 2-(4-pyridyl)-benzimidazole for mild steel in hydrochloric acid," Corrosion Science (2012) 61: 1-9.

PCT International Search Report and Written Opinion for PCT/US2018/059947, dated Feb. 20, 2019, 17 pages.

* cited by examiner

ONE-POT HOMOGENEOUS PROCESS FOR THE LARGE SCALE MANUFACTURE OF 2-SUBSTITUTED BENZIMIDAZOLES

BACKGROUND

1. Field of the Invention

The present disclosure generally relates to the synthesis of 2-substituted benzimidazoles and compositions thereof. More particularly, the disclosure pertains to a homogenous process for synthesizing 2-substituted benzimidazoles and their use, for example, as corrosion inhibitors.

2. Description of the Related Art

Benzimidazoles can be made using different synthetic pathways. One common pathway is an acid catalyzed condensation reaction between a diamine and a carboxylic acid. This pathway is mainly focused towards obtaining solid benzimidazoles as isolated final products in moderate to good yields.

These benzimidazoles are predominantly synthesized in mineral acids, and the final product is precipitated by adjusting the pH to 7 or 8 using a base. The precipitated product is isolated by filtration and dried in an oven. Prior art synthetic methods suffer from several disadvantages, such as: 1) prolonged reaction and process times resulting in low throughput per batch; 2) yield loss from workup and isolation steps; 3) isolation and subsequent drying steps require installation of special equipment, thereby incurring a significant capital investment; 4) handling of solid product, both as a wetcake and as dry powder, involves significant material handling challenges resulting in yield loss; and 5) final solid product needs to be dried prior to re-dissolution in a solvent for use in certain applications, such as anti-corrosion.

Other uses for benzimidazoles include applications in pharmaceuticals and agrochemicals. Polybenzimidazoles are known for their high strength and high temperature performance. Polybenzimidazoles find use in semiconductors, contact seals, wafer carriers, insulator bushings, thermal insulators, light emitting diodes, solar cells, fuel cells, and high performance protective apparel. Other uses include applications in the petrochemical and aerospace industries.

BRIEF SUMMARY

In some embodiments, a composition is disclosed that includes a compound or salt thereof of formula (I), an acid, and a polar aprotic solvent;

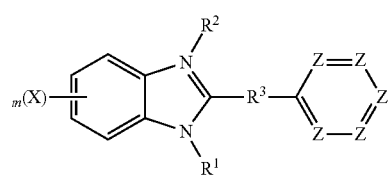

wherein X is independently hydrogen, halogen, or a substituted or unsubstituted $C_{1-5}$ alkyl group, and m is 1, 2, 3, or 4; $R^1$ is hydrogen, a substituted or unsubstituted $C_1$-$C_{12}$ alkyl group, or a substituted or unsubstituted $C_4$-$C_6$ aryl group; $R^2$ is absent, hydrogen, a substituted or unsubstituted $C_1$-$C_{12}$ alkyl group, or a substituted or unsubstituted $C_4$-$C_6$ aryl group; $R^3$ is a bond or $CHR^4$; $R^4$ is hydrogen, halogen, $NR^5R^6$, or $OR^5$; wherein $R^5$ and $R^6$ are each independently hydrogen, a substituted or unsubstituted $C_1$-$C_{12}$ alkyl group, or a substituted or unsubstituted $C_4$-$C_6$ aryl group; and Z is independently nitrogen, CX, or $N^+R^5$.

In some embodiments, the composition may include water.

In some embodiments, the composition may be a homogenous liquid.

In some embodiments, X is independently hydrogen or halogen, $R^1$ is hydrogen, $R^2$ is absent, and $R^3$ is $CHR^4$.

In some embodiments, at least one Z is nitrogen.

In some embodiments, $R^3$ is a bond and at least one Z is nitrogen.

In some embodiments, the compound or salt thereof is of formula (II)

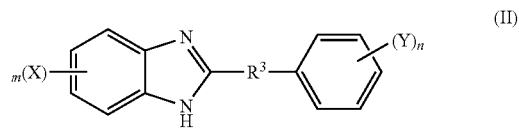

wherein Y is independently hydrogen, halogen, or a $C_{1-5}$ alkyl group; and n is 1, 2, 3, 4, or 5.

In some embodiments, the acid may be a strong inorganic acid, a strong organic acid, or any combination thereof.

In some embodiments, the acid may be selected from sulfuric acid, hydrochloric acid, nitric acid, methanesulfonic acid, phosphoric acid, sulfamic acid, aminomethylphosphonic acid, p-toluenesulfonic acid, and any combination thereof.

In some embodiments, the polar aprotic solvent may be selected from acetonitrile, N,N-dimethylformamide, acetone, dimethylsulfoxide, sulfolane, N-methylpyrrolidinone, methylsulfonylmethane, chlorobenzene, o-dichlorobenzene, nitromethane, an ionic liquid, and any combination thereof.

In some embodiments, the composition may include a high temperature stable phase transfer catalyst.

In some embodiments, the high temperature stable phase transfer catalyst may be selected from the group consisting of an alkyl guanidinium salt, an aryl guanidinium salt, an alkyl phosphonium salt, an aryl phosphonium salt, a peralkylated phosphazenium salt, and any combination thereof.

In other embodiments, a process for making a compound or salt thereof of formula (V) is disclosed.

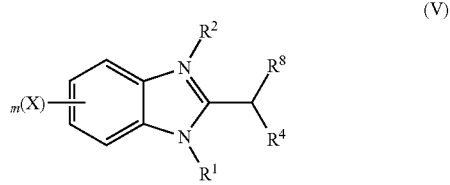

The process may include heating a mixture comprising a compound or salt thereof of formula (III), a compound or salt thereof of formula (IV), an acid, a polar aprotic solvent, and a high temperature stable phase transfer catalyst,

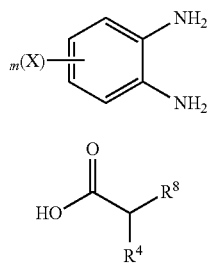

(III)

(IV)

wherein X is independently hydrogen, halogen, or a $C_{1-5}$ alkyl group, and m is 1, 2, 3, or 4; $R^1$ is hydrogen, a substituted or unsubstituted $C_1$-$C_{12}$ alkyl group, a substituted or unsubstituted $C_4$-$C_6$ aryl group; $R^2$ is absent, hydrogen, a substituted or unsubstituted $C_1$-$C_{12}$ alkyl group, a substituted or unsubstituted $C_4$-$C_6$ aryl group; $R^4$ is hydrogen, halogen, $NR^5R^6$, or $OR^5$; wherein $R^5$ and $R^6$ are each independently hydrogen, a substituted or unsubstituted $C_1$-$C_{12}$ alkyl group or a substituted or unsubstituted $C_4$-$C_6$ aryl group; and $R^8$ is hydrogen, halogen, a substituted or unsubstituted $C_1$-$C_{12}$ alkyl group, a substituted or unsubstituted $C_5$-$C_6$ heteroaryl group, a substituted or unsubstituted $C_4$-$C_6$ aryl group, or a substituted or unsubstituted $C_3$-$C_{12}$ cycloalkyl group.

In some embodiments, the mixture may be heated to a temperature of from about 80° C. to about 160° C.

In some embodiments, the mixture may be heated for a period of time ranging from about 30 minutes to about 12 hours.

In some embodiments, the mixture may include an actives concentration of from about 1 to about 50% by weight.

In some embodiments, the process may include adding to the mixture a carboxylic acid.

In certain embodiments, a use of any composition disclosed herein for inhibiting corrosion is disclosed.

In certain embodiments, a composition is disclosed that may be prepared according to any process disclosed herein.

In other embodiments, a process for preparing a polybenzimidazole is disclosed. The process may include heating a mixture comprising diphenyl isophthalate and 3,3',4,4'-tetraaminodiphenyl, an acid, a polar aprotic solvent, and a high temperature stable phase transfer catalyst.

In other embodiments, a method of inhibiting corrosion is disclosed that may include adding any composition disclosed herein to an industrial water system that includes a metallic surface.

The foregoing has outlined rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific embodiments disclosed may be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

DETAILED DESCRIPTION

Various embodiments are described below. The relationship and functioning of the various elements of the embodiments may better be understood by reference to the following detailed description. However, embodiments are not limited to those illustrated below. In certain instances, details may have been omitted that are not necessary for an understanding of embodiments disclosed herein.

"Alkyl" refers to a straight-chain or branched alkyl substituent. Examples of such substituents include methyl, ethyl, propyl, isopropyl, n-butyl, sec-butyl, isobutyl, tert-butyl, pentyl, isoamyl, hexyl, and the like.

"Aryl" refers to an unsubstituted or substituted aromatic carbocyclic substituent, as commonly understood in the art, and the term "$C_6$-$C_{10}$ aryl" includes phenyl and naphthyl. It is understood that the term aryl applies to cyclic substituents that are planar and comprise 4n+2n electrons, according to Huckel's Rule.

"Cycloalkyl" refers to a cyclic alkyl substituent containing from, for example, about 3 to about 8 carbon atoms, preferably from about 4 to about 7 carbon atoms, and more preferably from about 4 to about 6 carbon atoms. Examples of such substituents include cyclopropyl, cyclobutyl, cyclopentyl, cyclohexyl, cycloheptyl, cyclooctyl, and the like. The cyclic alkyl groups may be unsubstituted or further substituted with alkyl groups, such as methyl groups, ethyl groups, and the like.

"Halogen" or "halo" refers to F, Cl, Br, and I.

"Heteroaryl" refers to a monocyclic or bicyclic 5- or 6-membered ring system, wherein the heteroaryl group is unsaturated and satisfies Huckel's rule. Non-limiting examples of heteroaryl groups include furanyl, thiophenyl, pyrrolyl, pyrazolyl, imidazolyl, 1,2,3-triazolyl, 1,2,4-triazolyl, isoxazolyl, oxazolyl, isothiazolyl, thiazolyl, 1,3,4-oxadiazol-2-yl, 1,2,4-oxadiazol-2-yl, 5-methyl-1,3,4-oxadiazole, 3-methyl-1,2,4-oxadiazole, pyridinyl, pyrimidinyl, pyrazinyl, triazinyl, benzofuranyl, benzothiophenyl, indolyl, quinolinyl, isoquinolinyl, benzimidazolyl, benzoxazolinyl, benzothiazolinyl, quinazolinyl, and the like.

"Oxo" refers to an oxygen atom double-bonded to a carbon atom.

Compounds of the present disclosure may be substituted with suitable substituents. The term "suitable substituent," as used herein, is intended to mean a chemically acceptable functional group, preferably a moiety that does not negate the activity of the compounds. Such suitable substituents include, but are not limited to, halo groups, perfluoroalkyl groups, perfluoro-alkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, HO—(C═O)— groups, heterocylic groups, cycloalkyl groups, amino groups, alkyl- and dialkylamino groups, carbamoyl groups, alkylcarbonyl groups, alkoxycarbonyl groups, alkylaminocarbonyl groups, dialkylamino carbonyl groups, arylcarbonyl groups, aryloxy-carbonyl groups, alkylsulfonyl groups, and arylsulfonyl groups. In some embodiments, suitable substituents may include halogen, an unsubstituted $C_1$-$C_{12}$ alkyl group, an unsubstituted $C_4$-$C_6$ aryl group, or an unsubstituted alkoxy group. Those skilled in the art will appreciate that many substituents can be substituted by additional substituents.

In some embodiments, a composition is disclosed that may include a compound or salt thereof of formula (I), an acid, and a polar aprotic solvent. The compound of formula (I) has the formula shown below

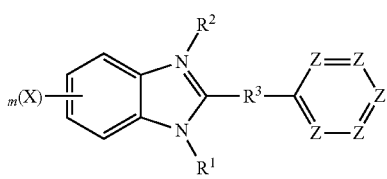

(I)

In some embodiments, X is independently hydrogen, halogen, or a substituted or unsubstituted $C_{1-5}$ alkyl group, and m may be 1, 2, 3, or 4. In some embodiments, $R^1$ may be hydrogen, a substituted or unsubstituted $C_1$-$C_{12}$ alkyl group, or a substituted or unsubstituted $C_4$-$C_6$ aryl group. In some embodiments, $R^2$ may be absent, hydrogen, a substituted or unsubstituted $C_1$-$C_{12}$ alkyl group, or a substituted or unsubstituted $C_4$-$C_6$ aryl group. In some embodiments, $R^3$ may be a bond or $CHR^4$. In some embodiments, $R^4$ may be hydrogen, halogen, $NR^5R^6$, or $OR^5$. In some embodiments, $R^5$ and $R^6$ are each independently hydrogen, a substituted or unsubstituted $C_1$-$C_{12}$ alkyl group, or a substituted or unsubstituted $C_4$-$C_6$ aryl group.

The X substituent or substituents can occupy any available position on the benzimidazole ring. Thus, in certain embodiments, the X substituent or substituents can be located at the 4-position, 5-position, 6-position, and/or 7-position of the benzimidazole. In certain embodiments, the X substituent is at the 5-position.

The number of X substituents, m, can be 1, 2, 3, or 4. If m is 2, 3, or 4, the X substituents can occupy any open position and can be positioned ortho-, meta-, or para- to each other.

In certain embodiments, the salt of the compound of formula (I) may be any salt, such as a chloride salt, bromide salt, iodide salt, sulfate salt, fluoride salt, perchlorate salt, acetate salt, trifluoroacetate salt, phosphate salt, nitrate salt, carbonate salt, bicarbonate salt, formate salt, chlorate salt, bromated salt, chlorite salt, thiosulfate salt, oxalate salt, cyanide salt, cyanate salt, tetrafluoroborate salt, and the like. In some embodiments, salt of the compound of formula (I) may be a hydrochloride or sulfate salt.

In some embodiments, Z is independently nitrogen, CX, or $N^+R^5$.

In some embodiments, Z is CX.

In some embodiments, X is hydrogen and m is 4.

In some embodiments, $R^1$ is hydrogen.

In some embodiments, $R^2$ is absent.

In some embodiments, $R^3$ is a bond.

In some embodiments, $R^3$ is $CHR^4$.

In some embodiments, $R^4$ is hydrogen.

In some embodiments, $R^4$ is halogen.

In some embodiments, $R^4$ is $NR^5R^6$.

In some embodiments, $R^4$ is $OR^5$.

In some embodiments, $R^5$ is a substituted or unsubstituted $C_1$-$C_{12}$ alkyl group.

In some embodiments, $R^5$ is hydrogen.

In some embodiments, $R^5$ is a substituted or unsubstituted $C_4$-$C_6$ aryl group.

In some embodiments, one Z is nitrogen and the rest are CX.

In some embodiments, at least two Zs are nitrogen and the rest are CX.

In some embodiments, $R^3$ is a bond and at least one Z is nitrogen.

In some embodiments, X is independently hydrogen or halogen, $R^1$ is hydrogen, $R^2$ is absent, and $R^3$ is $CHR^4$.

In some embodiments, the compound or salt thereof of formula (I) is

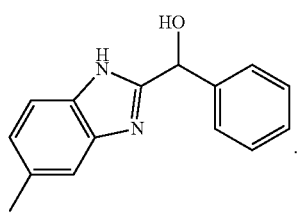 [SMILES: Cc1ccc2[nH]c(C(O)c3ccccc3)nc2c1]

In some embodiments, the compound or salt thereof of formula (I) is

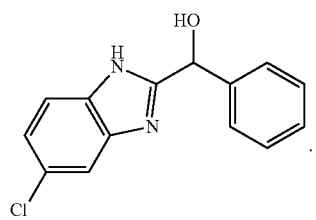 [SMILES: OC(c1ccccc1)c1nc2cc(Cl)ccc2[nH]1]

In some embodiments, the compound or salt thereof of formula (I) is

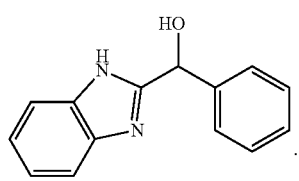 [SMILES: OC(c1ccccc1)c1nc2ccccc2[nH]1]

In some embodiments, the compound or salt thereof of formula (I) is

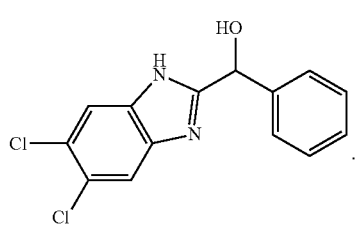 [SMILES: OC(c1ccccc1)c1nc2cc(Cl)c(Cl)cc2[nH]1]

In some embodiments, the compound or salt thereof of formula (I) is

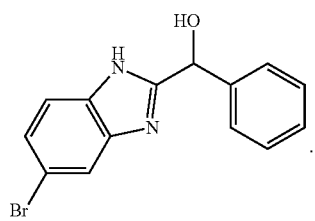

In some embodiments, the compound or salt thereof of formula (I) is

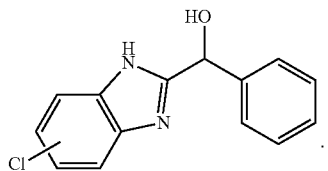

In some embodiments, the compound or salt thereof of formula (I) is

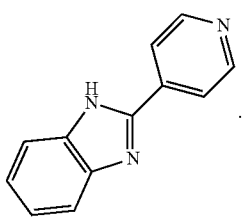 [SMILES: c1ccc2[nH]c(-c3ccncc3)nc2c1]

In some embodiments, the compound or salt thereof of formula (I) is

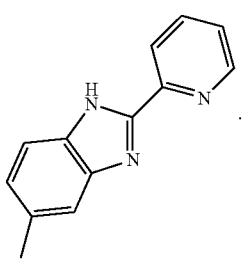 [SMILES: Cc1ccc2[nH]c(-c3ccccn3)nc2c1]

In some embodiments, the compound or salt thereof of formula (I) is

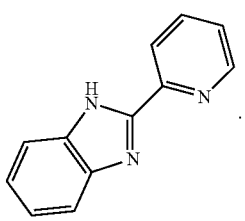 [SMILES: c1ccc(-c2nc3ccccc3[nH]2)nc1]

In some embodiments, the compound or salt thereof of formula (I) is

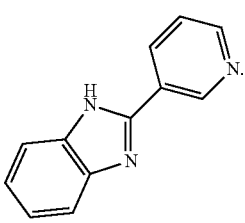 [SMILES: c1cncc(-c2nc3ccccc3[nH]2)c1]

In some embodiments, the compound or salt thereof of formula (I) is

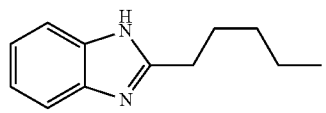

In some embodiments, the compound or salt thereof of formula (I) is

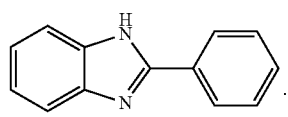

In some embodiments, the composition may include a compound or salt thereof of formula (Ia),

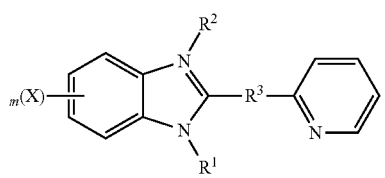

(Ia)

where X is independently hydrogen, halogen, or a substituted or unsubstituted $C_{1-5}$ alkyl group, and m is 1, 2, 3, or 4; $R^1$ is hydrogen, a substituted or unsubstituted $C_1$-$C_{12}$ alkyl group, or a substituted or unsubstituted $C_4$-$C_6$ aryl group; $R^2$ is absent, hydrogen, a substituted or unsubstituted $C_1$-$C_{12}$ alkyl group, or a substituted or unsubstituted $C_4$-$C_6$ aryl group; and $R^3$ is a bond or $CHR^4$.

In some embodiments, the compound or salt thereof is of formula (II),

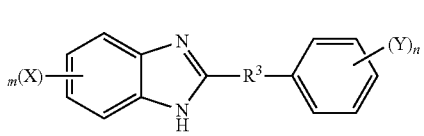

(II)

where X, m, and $R^3$ X is independently hydrogen, halogen, or a substituted or unsubstituted $C_{1-5}$ alkyl group; m is 1, 2, 3, or 4; $R^3$ is a bond or $CHR^4$; Y is independently hydrogen, halogen, or a $C_{1-5}$ alkyl group; and n is 1, 2, 3, 4, or 5.

In some embodiments, Y is hydrogen.

In some embodiments, Y is independently hydrogen and halogen.

As described herein, m can be 1, 2, 3, or 4. If m is 2, 3, or 4, the X substituents can occupy any open position and can be positioned ortho-, meta-, or para- to each other. The number of Y substituents, n, can be 1, 2, 3, or 4. If n is 2, 3, or 4, the Y substituents can occupy any open position and can be positioned ortho-, meta-, or para- to each other.

In some embodiments, the concentration of the compound or salt thereof of formula (I), formula (Ia), or formula (II) in the composition may range from about 1 wt % to about 50 wt %, about 5 wt % to about 50 wt %, about 10 wt % to about 50 wt %, about 15 wt % to about 50 wt %, about 20 wt % to about 50 wt %, about 20 wt % to about 45 wt %, about 25 wt % to about 45 wt %, or about 25 wt % to about 40 wt %.

In some embodiments, the acid may be a strong inorganic acid, a strong organic acid, or any combination thereof. In some embodiments, the acid may be a strong inorganic acid. In some embodiments, the acid may be a strong organic acid. As used herein, "strong" refers to acids having a pKa of less than about 1. In some embodiments, the acid may be selected from sulfuric acid, hydrochloric acid, nitric acid, methanesulfonic acid, phosphoric acid, sulfamic acid, aminomethylphosphonic acid, p-toluenesulfonic acid, and any combination thereof.

In some embodiments, the acid may be sulfuric acid.
In some embodiments, the acid may be hydrochloric acid.
In some embodiments, the acid may be nitric acid.
In some embodiments, the acid may be methanesulfonic acid.
In some embodiments, the acid may be phosphoric acid.
In some embodiments, the acid may be sulfamic acid.
In some embodiments, the acid may be aminomethylphosphonic acid.
In some embodiments, the acid may be p-toluenesulfonic acid.

In some embodiments, the polar aprotic solvent may be selected from acetonitrile, N,N-dimethylformamide, acetone, dimethylsulfoxide, sulfolane, N-methylpyrrolidinone, methylsulfonylmethane, chlorobenzene, o-dichlorobenzene, nitromethane, an ionic liquid, and any combination thereof.

In some embodiments, the polar aprotic solvent may be acetonitrile.
In some embodiments, the polar aprotic solvent may be N,N-dimethylformamide.
In some embodiments, the polar aprotic solvent may be acetone.
In some embodiments, the polar aprotic solvent may be dimethylsulfoxide.
In some embodiments, the polar aprotic solvent may be sulfolane.
In some embodiments, the polar aprotic solvent may be N-methylpyrrolidinone.
In some embodiments, the polar aprotic solvent may be methylsulfonylmethane.
In some embodiments, the polar aprotic solvent may be chlorobenzene.
In some embodiments, the polar aprotic solvent may be o-dichlorobenzene.
In some embodiments, the polar aprotic solvent may be nitromethane.
In some embodiments, the polar aprotic solvent may be an ionic liquid.

In some embodiments, the composition may include a high temperature stable phase transfer catalyst.

In some embodiments, the high temperature stable phase transfer catalyst is selected from the group consisting of an alkyl guanidinium salt, an aryl guanidinium salt, an alkyl phosphonium salt, an aryl phosphonium salt, a peralkylated phosphazenium salt, and any combination thereof. Examples of high temperature stable phase transfer catalysts include, but are not limited to, hexaethyl guanidinium chloride, tetraphenyl phosphonium bromide, hexaalkyl phosphonium salts, hexadecyltributylphosphonium bromide, or any combinations thereof.

In some embodiments, the composition may include water.

In some embodiments, the composition may be a homogenous mixture. In some embodiments, the composition may be a solution.

In some embodiments, the composition may include a phenylenediamine compound. In some embodiments, the composition may include a phenylenediamine compound. If the composition includes a phenylenediamine compound, it is present in the composition in an amount of about 0.0001 wt % to about 0.1 wt %. In some embodiments, the amount of phenylenediamine compound in the composition may be less than about 0.1 wt %. In some embodiments, the amount of phenylenediamine compound in the composition may be less than about 0.9 wt %, about 0.8 wt %, about 0.7 wt %, about 0.6 wt %, about 0.5 wt %, about 0.4 wt %, or about 0.3 wt %.

In other embodiments, a process for making a compound or salt thereof of formula (V) is disclosed.

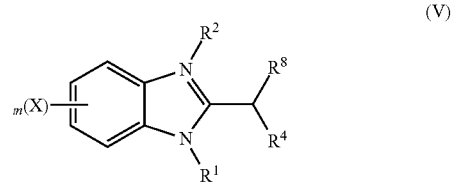

(V)

The process may include heating a mixture that includes a compound or salt thereof of formula (III), a compound or salt thereof of formula (IV), an acid, a polar aprotic solvent, and a high temperature stable phase transfer catalyst.

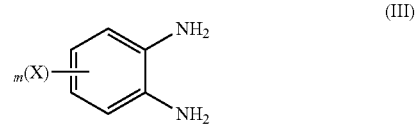

(III)

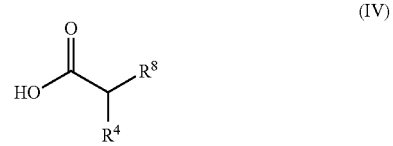

(IV)

For formulas (III-V), X is independently hydrogen, halogen, or a substituted or unsubstituted $C_{1-5}$ alkyl group, and m is 1, 2, 3, or 4; $R^1$ is hydrogen, a substituted or unsubstituted $C_1$-$C_{12}$ alkyl group, or a substituted or unsubstituted $C_4$-$C_6$ aryl group; $R^2$ is absent, hydrogen, a substituted or unsubstituted $C_1$-$C_{12}$ alkyl group, or a substituted or unsubstituted $C_4$-$C_6$ aryl group; $R^4$ is hydrogen, halogen, $NR^5R^6$, or $OR^5$; and Fe may be hydrogen, halogen, a substituted or unsubstituted $C_1$-$C_{12}$ alkyl group, a substituted or unsubstituted $C_5$-$C_6$ heteroaryl group, a substituted or unsubstituted $C_4$-$C_6$ aryl group, or a substituted or unsubstituted $C_3$-$C_{12}$ cycloalkyl group. $R^5$ and $R^6$ are each independently hydrogen, a substituted or unsubstituted $C_1$-$C_{12}$ alkyl group, or a substituted or unsubstituted $C_4$-$C_6$ aryl group.

In some embodiments, Fe is a substituted or unsubstituted $C_5$-$C_6$ heteroaryl group.
In some embodiments, Fe is a substituted or unsubstituted $C_5$-$C_6$ heteroaryl group or a substituted or unsubstituted $C_4$-$C_6$ aryl group.
In some embodiments, Fe is a substituted or unsubstituted $C_4$-$C_6$ aryl group.

In some embodiments, Fe is a substituted or unsubstituted $C_6$ heteroaryl group.

In some embodiments, Fe is a substituted or unsubstituted $C_6$ aryl group.

In some embodiments, the reaction product of the compounds of formulae (III) and (IV) may be further reacted in a post-modification step to add substituents other than hydrogen for $R^1$ and substituents for $R^2$.

The synthetic processes disclosed herein have many advantages over the prior art. The final product can be obtained in higher yields as compared to conventional synthesis methods. The final product may also be in a homogeneous liquid form, thereby facilitating product transfer and formulation while minimizing yield losses. Since the final product may be in homogeneous liquid form, solids isolation processes and equipment are no longer required resulting in significant cost reductions.

In certain embodiments, a process for making a compound or salt thereof of formula (I) is disclosed.

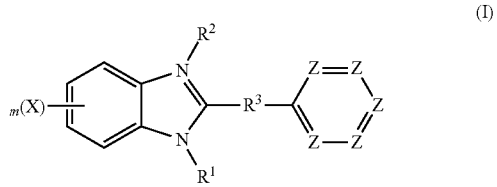
(I)

The process may include heating a mixture that includes a compound or salt thereof of formula (III), a compound or salt thereof of formula (VI), an acid, a polar aprotic solvent, and a high temperature stable phase transfer catalyst,

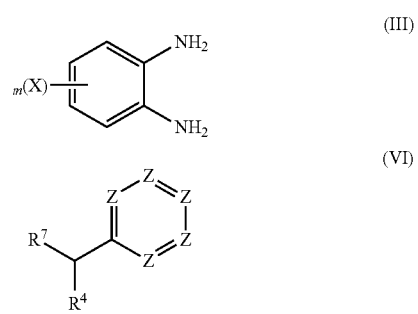
(III)

(VI)

For formulas (I), (III), and (VI), X is independently hydrogen, halogen, or a substituted or unsubstituted $C_{1-5}$ alkyl group, and m is 1, 2, 3, or 4; $R^1$ is hydrogen, a substituted or unsubstituted $C_1$-$C_{12}$ alkyl group, or a substituted or unsubstituted $C_4$-$C_6$ aryl group; $R^2$ is absent, hydrogen, a substituted or unsubstituted $C_1$-$C_{12}$ alkyl group, or a substituted or unsubstituted $C_4$-$C_6$ aryl group; $R^3$ is a bond or $CHR^4$; $R^4$ is hydrogen, halogen, $NR^5R^6$, or $OR^5$, where $R^5$ and $R^6$ are each independently hydrogen, a substituted or unsubstituted $C_1$-$C_{12}$ alkyl group, or a substituted or unsubstituted $C_4$-$C_6$ aryl group; and Z is independently nitrogen, CX, or $N^+R^5$. In some embodiments, $R^7$ is oxo or COOH.

In some embodiments, $R^7$ is COOH.

In some embodiments, $R^7$ is oxo.

Any acid described in the present disclosure and any equivalents can be used in the process of making compounds or salts of formulas (I) and (V).

In some embodiments, the concentration of acid in the mixture or composition may range from about 1 wt % to about 70 wt %. In some embodiments, the concentration of acid in the mixture or composition may range from about 1 wt % to about 60 wt %, about 1 wt % to about 50 wt %, about 1 wt % to about 40 wt %, about 1 wt % to about 30 wt %, about 5 wt % to about 60 wt %, about 5 wt % to about 50 wt %, about 5 wt % to about 40 wt %, or about 5 wt % to about 30 wt %.

Any polar aprotic solvent described in the present disclosure and any equivalents can be used in the process of making compounds or salts of formulas (I) and (V).

In some embodiments, the concentration of polar aprotic solvent in the mixture or composition may range from about 0.001 wt % to about 30 wt %. In some embodiments, the concentration of polar aprotic solvent in the mixture may range from about 0.001 wt % to about 25 wt %, about 0.001 wt % to about 20 wt %, about 0.01 wt % to about 25 wt %, about 0.1 wt % to about 25 wt %, about 0.5 wt % to about 25 wt %, about 1 wt % to about 25 wt %, about 1 wt % to about 20 wt %, or about 1 wt % to about 25 wt %. In some embodiments, the concentration of polar aprotic solvent in the mixture may be 1 wt %, 5 wt %, or 10 wt %.

Any high temperature stable phase transfer catalyst described in the present disclosure and any equivalents can be used in the process of making compounds or salts of formulas (I) and (V).

In some embodiments, the concentration of high temperature stable phase transfer catalyst in the mixture or composition may range from about 0.001 wt % to about 30 wt %. In some embodiments, the concentration of high temperature stable phase transfer catalyst in the mixture or composition may range from about 0.001 wt % to about 25 wt %, about 0.001 wt % to about 20 wt %, about 0.01 wt % to about 25 wt %, about 0.1 wt % to about 25 wt %, about 0.5 wt % to about 25 wt %, about 1 wt % to about 25 wt %, about 1 wt % to about 20 wt %, or about 1 wt % to about 25 wt %. In some embodiments, the concentration of polar aprotic solvent in the mixture may be 1 wt %, 5 wt %, or 10 wt %.

In some embodiments, the process of making a compound or salt thereof of formula (I) or (V) may include heating the mixture to a temperature of from about 80° C. to about 160° C. In some embodiments, the mixture may be heated to a temperature of from about 80° C. to about 120° C., about 90° C. to about 120° C., or about 90° C. to about 110° C. The mixture can be heated using any means suitable for raising the temperature to the appropriate level. Heating systems may be fuel-, electricity-, or steam-based. For example, steam could be passed through tubes that contact the mixture.

In some embodiments, the mixture may be heated for a period of time ranging from about 30 minutes to about 12 hours. In some embodiments, the mixture may be heated for a period of time ranging from about 1 hour to about 12 hours, about 2 hours to about 12 hours, about 2 hour to about 10 hours, about 4 hour to about 10 hours, or about 5 hour to about 10 hours.

In some embodiments, the mixture may have an actives concentration of from about 1 to about 50% by weight, where "actives concentration" refers to the concentration of compounds of formula (III) and formula (IV) or compounds of formula (III) and formula (VI). In some embodiments, the mixture may have an actives concentration of from about 10 wt % to about 50 wt %, about 20 wt % to about 50 wt %, about 20 wt % to about 45 wt %, about 25 wt % to about 45 wt %, or about 25 wt % to about 40 wt %.

In some embodiments, the processes described in the present disclosure may include adding a carboxylic acid to the mixture after the heating step. As used herein, "carboxylic acid" refers to an organic compound that contains a carboxyl group. In some embodiments, the carboxylic acid may be a substituted or unsubstituted $C_1$-$C_{32}$ alkyl carboxylic acid. In some embodiments, the carboxylic acid reacts with unreacted compounds of formula (III). In certain embodiments, the carboxylic acid may be acetic acid, or formic acid. Other carboxylic acids that may be used include, but are limited to butanoic acid, carbonic acid, propionic acid, pentanoic acid, hexanoic acid, heptanoic acid, octanoic acid, nonanoic acid, glycolic acid, and the like. The amount of carboxylic acid added to the mixture may be from about 0.01 wt % to about 10 wt %. In some embodiments, the amount of carboxylic acid added to the mixture may be from about 0.1 wt % to about 5 wt %, about 1 wt % to about 5 wt %, or about 1 wt % to about 4 wt %. In some embodiments, the amount of carboxylic acid added to the mixture may be about 1 wt %, about 2 wt %, about 3 wt %, about 4 wt %, about 5 wt %, about 6 wt %, about 7 wt %, about 8 wt %, about 9 wt %, or about 10 wt %.

In some embodiments, a composition is disclosed that is prepared according to the processes described in this disclosure. The processes of making a compound or salt of formula (I) or (V) may produce a homogenous composition that can be used for corrosion inhibition without further purification.

In some embodiments, the compositions of this disclosure can be used in pharmaceuticals. In some embodiments, the compositions of this disclosure can be used in agrochemicals. In some embodiments, the compositions of this disclosure can be used for inhibiting corrosion.

In some embodiments, a method of preventing corrosion is disclosed.

The disclosure provides methods of using heterocyclic compounds and formulations comprising heterocyclic compounds that are particularly useful for inhibiting corrosion of metallic components in industrial water systems. Adding to an aqueous system a benzimidazole capable of undergoing chelation with a metal provides excellent metal corrosion resistance. In particular, adding benzimidazoles substituted with a 2-pyridyl or a benzyl alcohol to an aqueous system in contact with a metal surface leads to excellent corrosion inhibition for metals such as copper. Moreover, while benzotriazoles and benzimidazoles are generally unstable in the presence of oxidizing halogen compounds, the compounds of the present disclosure are capable of undergoing 1,2-chelation with a metal to impart exemplary protection of metal in the presence of oxidizing halogen compounds. In particular, 2-(2-pyridyl)benzimidazoles provide greater protection against corrosion than benzimidazole, 2-phenylbenzimidazole, and tolyltriazole in the presence of oxidizing halogen compounds. While not wishing to be bound by any particular theory, it is believed that the compounds of the present disclosure form a protective film that is essentially impenetrable by common oxidizing halogen compounds due to bidentate chelation of the corrosion inhibitor with the metal surface. Thus, in certain embodiments, the methods of the present disclosure provide protection against metal corrosion in aqueous systems which employ oxidizing halogen compounds as biocides.

In some embodiments, the disclosure provides a method for inhibiting corrosion of a metal surface in contact with an aqueous system. The method may include adding to the aqueous system any composition described in the present disclosure. For example, the composition may include a compound of formula (I), an acid, and a polar aprotic solvent.

"Industrial water system" means any system that circulates water as its primary ingredient. Non-limiting examples of "industrial water systems" include cooling systems, boiler systems, heating systems, membrane systems, papermaking systems, or any other systems that circulate water.

The compounds of formulae (I), (Ia), and (II) may provide corrosion protection for any metal or metal alloy including, but not limited to, copper, iron, silver, steel (e.g., galvanized steel), and aluminum. In certain embodiments, a compound of formula (I), (Ia), or (II) is added to an aqueous system in contact with a metal surface comprising copper to inhibit metal corrosion. In certain embodiments, a compound of formula (I), (Ia), or (II) is added to an aqueous system in contact with a metal surface comprising a copper alloy to inhibit metal corrosion. In certain embodiments, copper complexes with one or more heteroatoms in a compound of formula (I), (Ia), or (II). In certain embodiments, copper complexes with one or more heteroatoms in a compound of formula (I), (Ia), or (II). Copper has a wide-range of applications, including use as copper piping and tubing in plumbing and industrial machinery. Copper and copper alloys are well known for their use in cooling water and boiler water systems.

The compounds of formulae (I), (Ia), and (II) can be used to protect any copper alloy, including bronze and brass. Bronze commonly comprises copper and tin, but may comprise other elements including aluminum, manganese, silicon, arsenic, and phosphorus. Brass comprises copper and zinc, and is commonly used in piping in water boiler systems. In certain embodiments, a compound of formula (I), (Ia), or (II) is added to an aqueous system in contact with a metal surface comprising bronze to inhibit metal corrosion. In certain embodiments, a compound of formula (I), (Ia), or (II) is added to an aqueous system in contact with a metal surface comprising brass, for example admiralty brass, to inhibit metal corrosion. In certain embodiments, a compound of formula (I), (Ia), or (II) is added to an aqueous system in contact with a metal surface comprising a copper-nickel alloy to inhibit metal corrosion.

In certain embodiments, a compound of formula (I), (Ia), or (II) inhibits the corrosion of mild steel. In certain embodiments, a compound of formula (I), (Ia), or (II) inhibits the corrosion of metal alloys including, but not limited to, galvanized steel, stainless steel, cast iron, nickel, and combinations thereof. While not wishing to be bound by any particular theory, it is postulated that the compounds of formulae (I), (Ia), and (II) inactivate Cu (II) in solution, preventing the occurrence of galvanic cells on the steel surface. Thus, in certain embodiments, a compound of formula (I), (Ia), or (II) inhibits pitting corrosion of mild steel.

While the compounds of formulae (I), (Ia), and (II) can be added to an aqueous system at any dosage rate, the compounds of formulae (I), (Ia), and (II) are generally added to an aqueous system at a dosage rate of from about 0.01 ppm to about 500 ppm. In certain embodiments, a compound of formula (I), (Ia), or (II) is added to an aqueous system at a dosage rate of from about 0.01 ppm to about 100 ppm. In certain embodiments, a compound of formula (I), (Ia), or (II) is added to an aqueous system at a dosage rate of from about 0.01 ppm to about 100 ppm, from about 0.01 ppm to about 75 ppm, from about 0.01 ppm to about 50 ppm, from about 0.01 ppm to about 25 ppm, from about 0.01 ppm to about 10 ppm, from about 0.01 ppm to about 5 ppm, from about 0.1 ppm to about 100 ppm, from about 0.1 ppm to about 75 ppm, from about 0.1 ppm to about 50 ppm, from about 0.1 ppm to about 25 ppm, from about 0.1 ppm to about 10 ppm, from about 0.1 ppm to about 5 ppm, from about 1 ppm to about 100 ppm, from about 1 ppm to about 75 ppm, from about 1 ppm to about 50 ppm, from about 1 ppm to about 25 ppm, from about 1 ppm to about 10 ppm, from about 5 ppm to about 100 ppm, from about 10 ppm to about 100 ppm, from about 25 ppm to about 100 ppm, from about 50 ppm to about 100 ppm, or from about 80 ppm to about 100 ppm.

In certain embodiments, the aqueous system is a cooling water system. The cooling water system can be a closed loop cooling water system or an open loop cooling water system. In certain embodiments, a compound of formula (I), (Ia), or (II) is added to a closed loop cooling water system at a dosage rate of from about 0.01 ppm to about 200 ppm. In certain embodiments, a compound of formula (I), (Ia), or (II) is added to an open loop cooling water system at a dosage rate of from about 0.01 ppm to about 20 ppm.

The compounds of formulae (I), (Ia), and (II) are contacted with a metal surface by any suitable method. In certain embodiments, a solution of a compound of formula (I), (Ia), or (II) is contacted with a metal surface by immersion, spraying, or other coating techniques. In certain embodiments, a solution of a compound of formula (I), (Ia), or (II) is introduced into the water of the aqueous system by any conventional method and is fed into the aqueous system on either a periodic or continuous basis.

In some embodiments, the compositions disclosed herein may include a fluorescent organic compound. In certain embodiments, the fluorescent organic compound may be selected from Rhodamine or derivatives thereof, an acridine dye, fluorescein or derivatives thereof, and combinations thereof. In certain embodiments, the compositions disclosed herein may include a fluorescent tagged polymer.

Those skilled in the art will appreciate that a compound of formula (I), (Ia), or (II) can be added to an aqueous system alone or in combination with other corrosion inhibitors or treatment chemicals. Multiple corrosion inhibitors can be dosed as a combined corrosion inhibitor formulation or each corrosion inhibitor can be added separately, including two or more compounds of formula (I), (Ia), and/or formula (II). Moreover, a compound of formula (I), (Ia), or (II) can be added to an aqueous system in combination with a variety of additional corrosion inhibitors including, but not limited to, triazoles, benzotriazoles (e.g., benzotriazole or tolyltriazole), benzimidazoles, orthophosphate, polyphosphates, phosphonates, molybdates, silicates, oximes, and nitrites. The compounds of formulae (I), (Ia), and (II) also can be added to an aqueous system in combination with a variety of additional additives, such as treatment polymers, anti-microbial agents, anti-scaling agents, colorants, fillers, buffers, surfactants, viscosity modifiers, chelating agents, dispersants, deodorants, masking agents, oxygen scavengers, and indicator dyes.

In other embodiments, a process for making polybenzimidazoles may include heating a mixture that has diphenyl isophthalate and 3,3',4,4'-tetraaminodiphenyl, an acid, a polar aprotic solvent, and a high temperature stable phase transfer catalyst. The acid, polar aprotic solvent, and high temperature stable phase transfer catalyst are as described in this disclosure.

Polybenzimidazoles are known for their high strength and high temperature performance. The polybenzimidazoles synthesized according to the processes disclosed herein can be used in, for example, semiconductors, contact seals, wafer carriers, insulator bushings, thermal insulators, light emitting diodes, solar cells, fuel cells, and high performance protective apparel. Other uses include applications in the petrochemical and aerospace industries.

EXAMPLES

Example 1

Several condensation reactions between 1,2-phenylenediamine (OPD) and DL-mandelic acid to produce (1H-benzo[d]imidazol-2-yl)(phenyl)methanol were carried out at 100-110° C. for about 6 to about 8 hours at about 30 to about 35 wt % actives. The effect of various additives, such as high temperature stable catalysts and co-solvents, on homogeneity of the reactions was studied and is listed in the Table 1.

TABLE 1

Various additives evaluated

| Additive | Solvent | Additive (wt %) | Actives (wt %) | Homogeneity |
|---|---|---|---|---|
| None | $H_2SO_4$ | 0 | 20-30 | No |
| HEG-Cl* | $H_2SO_4$ | 10 | 30 | No |
| HEG-Cl | Methanesulfonic acid | 10 | 35 | Yes (1 week**) |
| Sulfolane | $H_2SO_4$ | 15 | 30 | No |
| Sulfolane | Methanesulfonic acid | 15 | 35 | Yes |

*HEG-Cl = Hexaethyleneguanidinium chloride
**ambient temperature

Example 2

Several experiments were conducted using about 5 wt % sulfolane and about 3 wt % acetic acid in a post-treatment step. The HPLC analysis results are shown in Table 2. The results clearly show the decrease in the residual OPD concentration to be less than about 0.1 wt % and the resulting materials are regulatory compliant. Actives refers to the weight percent concentration of OPD and DL-mandelic acid at the beginning of the reaction.

Methanesulfonic acid, sulfolane and water were charged into a round bottom flask fitted with a magnetic stirrer, reflux condenser, and a temperature probe. To this, DL-Mandelic acid (1 equiv.) and 1,2-phenylenediamine (1 equiv.) were added and the contents of the flask were refluxed at about 100-110° C. for about 6-8 hours. After completion of the reaction, glacial acetic acid (3 wt %) was added and reflux was maintained for about 1-3 more hours. After the post-treatment, additional water was added to adjust the actives to about 20 wt %. Purity and residual OPD analysis was performed using NMR and HPLC.

TABLE 2

Homogeneity and conversion at different reaction conditions

| Run | Sulfolane (wt %) | Acetic acid (wt %) | Actives (wt %) | OPD (wt %) | Conversion (wt %) | Homogeneity |
|---|---|---|---|---|---|---|
| 1 | 5 | 3 | 20 | 0.02 | 97 | Yes |
| 2 | 2 | 3 | 20 | 0.02 | 97 | Yes |
| 3 | 5 | 3 | 20 | 0.09 | 91 | Yes |
| 4 | 5 | 3 | 20 | 0.04 | 97 | Yes |
| 5 | 5 | 3 | 20 | 0.05 | 96 | Yes |
| 6 | 5 | 3 | 20 | 0.02 | 97 | Yes |

Example 3: Synthesis of (1H-benzo[d]imidazol-2-yl)(phenyl)methanol

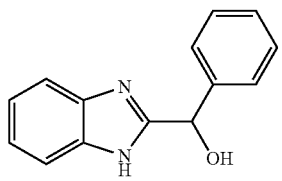 [SMILES: OC(c1ccccc1)c1nc2ccccc2[nH]1]

Methanesulfonic acid, sulfolane and water were charged into a flask fitted with a magnetic stirrer, reflux condenser, and a temperature probe. To this, o-phenylenediamine (about 12.96 g, 1 equiv.) and DL-Mandelic acid (about 19.15, 1.05 equiv.) were added and the contents of the flask were refluxed at about 110° C. After about 8 hours of reflux, about 3 g of acetic acid was added and reflux was maintained for an additional about 3 hours to obtain the title compound in about 97% yield.

Example 4: Synthesis of (5-chloro-1H-benzo[d]imidazol-2-yl)(phenyl)methanol

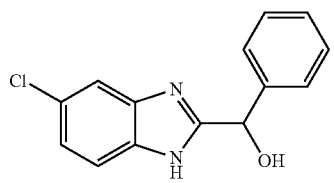

Methanesulfonic acid, sulfolane and water were charged into a flask fitted with a magnetic stirrer, reflux condenser, and a temperature probe. To this, 4-chlorobenzene-1,2-diamine (21.85 g, 1 equiv.) and DL-Mandelic acid (24.45, 1.05 equiv.) were added and the contents of the flask were refluxed at about 110° C. After about 8 hours of reflux, about 3 g of acetic acid was added and reflux was maintained for an additional about 3 hours to obtain the title compound in about 93% yield.

Example 5: (5-bromo-1H-benzo[d]imidazol-2-yl)(phenyl)methanol

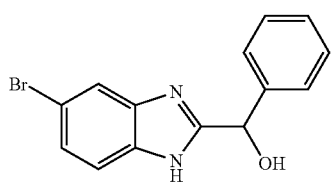 [SMILES: OC(c1ccccc1)c1nc2cc(Cl)ccc2[nH]1]

Methanesulfonic acid, sulfolane and water were charged into a flask fitted with a magnetic stirrer, reflux condenser, and a temperature probe. To this, 4-bromobenzene-1,2-diamine (22.08 g, 1 equiv.) and DL-Mandelic acid (19.15, 1.05 equiv.) were added and the contents of the flask were refluxed at about 110° C. After about 8 hours of reflux, about 3 g of acetic acid was added and reflux was maintained for additional about 3 hours to obtain the title compound in about 94% yield.

Example 6: (5-methyl-1H-benzo[d]imidazol-2-yl)(phenyl)methanol

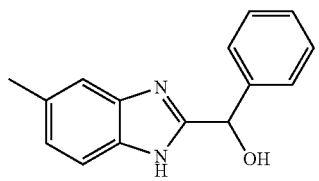 [SMILES: Cc1ccc2[nH]c(C(O)c3ccccc3)nc2c1]

Methanesulfonic acid, sulfolane and water were charged into a flask fitted with a magnetic stirrer, reflux condenser, and a temperature probe. To this, o-toluenediamine (18.3 g, 1 equiv.) and DL-Mandelic acid (23.94, 1.05 equiv.) were added and the contents of the flask were refluxed at about 110° C. After about 8 hours of reflux, about 3 g of acetic acid was added and reflux was maintained for additional about 3 hours to obtain the title compound in about 95% yield.

Prophetic Example 1: 2-(pyridin-2-yl)-1H-benzo[d]imidazole

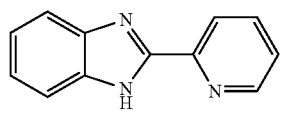 [SMILES: c1ccc(-c2nc3ccccc3[nH]2)nc1]

Methanesulfonic acid, sulfolane and water will be charged into a flask fitted with a magnetic stirrer, reflux condenser, and a temperature probe. To this, o-phenylenediamine (12.96 g, 1 equiv.) and Picolinic acid (15.51, 1.05 equiv.) will be added and the contents of the flask will be refluxed at about 110° C. After 8 h reflux time acetic acid (2 g) will be added and reflux will be maintained for additional about 3 hours to obtain the title compound.

Prophetic Example 2: 2-pentyl-1H-benzo[d]imidazole

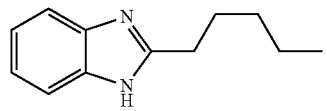

Methanesulfonic acid, sulfolane and water will be charged into a flask fitted with a magnetic stirrer, reflux condenser, and a temperature probe. To this, o-phenylenediamine (12.96 g, 1 equiv.) and hexanoic acid (15, 1.05 equiv.) will be added and the contents of the flask will be refluxed at about 110° C. After 8 h reflux time acetic acid (2 g) will be added and reflux will be maintained for an additional about 3 hours to obtain the title compound.

Prophetic Example 3:
2-phenyl-1H-benzo[d]imidazole

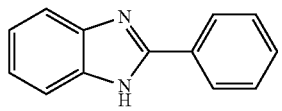 [SMILES: c1ccc(-c2nc3ccccc3[nH]2)cc1]

Methanesulfonic acid, sulfolane and water will be charged into a flask fitted with a magnetic stirrer, reflux condenser, and a temperature probe. To this, o-phenylenediamine (15.66 g, 1 equiv.) and benzoic acid (19 g, 1.05 equiv.) will be added and the contents of the flask will be refluxed at about 110° C. After 8 h reflux time acetic acid (2 g) will be added and reflux will be maintained for an additional about 3 hours to obtain the title compound.

Compound structures and chemical names were prepared and determined using ChemDraw Professional version 15.1.

Any composition disclosed herein may comprise, consist of, or consist essentially of any of the compounds/components disclosed herein. In accordance with the present disclosure, the phrases "consist essentially of," "consists essentially of," "consisting essentially of," and the like limit the scope of a claim to the specified materials or steps and those materials or steps that do not materially affect the basic and novel characteristic(s) of the claimed invention.

As used herein, the term "about" refers to the cited value being within the errors arising from the standard deviation found in their respective testing measurements, and if those errors cannot be determined, then "about" refers to within 10% of the cited value.

All of the compositions and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated. In addition, unless expressly stated to the contrary, use of the term "a" is intended to include "at least one" or "one or more." For example, "a compound" is intended to include "at least one compound" or "one or more compounds."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

What is claimed is:

1. A composition, comprising: a compound or salt thereof of formula (I), an acid, and a polar aprotic solvent;

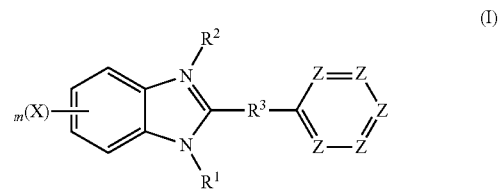

wherein
X is independently hydrogen, halogen, or a substituted or unsubstituted $C_{1-5}$ alkyl group, and m is 1, 2, 3, or 4;
$R^1$ is hydrogen, a substituted or unsubstituted $C_1$-$C_{12}$ alkyl group, or a substituted or unsubstituted $C_4$-$C_6$ aryl group;
$R^2$ is absent, hydrogen, a substituted or unsubstituted $C_1$-$C_{12}$ alkyl group, or a substituted or unsubstituted $C_4$-$C_6$ aryl group;
$R^3$ is a bond or $CHR^4$;
$R^4$ is hydrogen, halogen, $NR^5R^6$, or $OR^5$;
wherein $R^5$ and $R^6$ are each independently hydrogen, a substituted or unsubstituted $C_1$-$C_{12}$ alkyl group, or a substituted or unsubstituted $C_4$-$C_6$ aryl group; and
Z is independently nitrogen, CX, or $N^+R^5$;
wherein:
a concentration of the compound or salt of formula (I) in the composition is about 1 wt % to about 50 wt %;
a concentration of the acid in the composition is about 5 wt % to about 60 wt %; and
a concentration of the polar aprotic solvent in the composition is about 0.001 wt % to about 30 wt %.

2. The composition of claim 1, further comprising water.

3. The composition of claim 1, wherein
X is independently hydrogen or halogen;
$R^1$ is hydrogen;
$R^2$ is absent; and
$R^3$ is $CHR^4$.

4. The composition of claim 1, wherein at least one Z is nitrogen.

5. The composition of claim 1, wherein $R^3$ is a bond and at least one Z is nitrogen.

6. The composition of claim 1, wherein the compound or salt thereof is of formula (II)

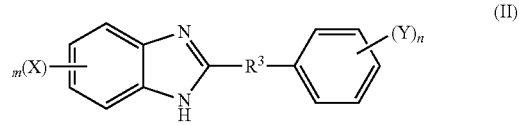

wherein:
Y is independently hydrogen, halogen, or a C1-5 alkyl group; and n is 1, 2, 3, 4, or 5.

7. The composition of claim 1, wherein the acid is selected from sulfuric acid, hydrochloric acid, nitric acid, methanesulfonic acid, phosphoric acid, sulfamic acid, aminomethylphosphonic acid, p-toluenesulfonic acid, and any combination thereof.

8. The composition of claim 1, wherein the polar aprotic solvent is selected from acetonitrile, N,N-dimethylformamide, acetone, dimethylsulfoxide, sulfolane, N-methylpyrrolidinone, methylsulfonylmethane, chlorobenzene, o-dichlorobenzene, nitromethane, an ionic liquid, and any combination thereof.

9. The composition of claim 1, wherein the composition is homogenous liquid.

10. The composition of claim 1, further comprising a high temperature stable phase transfer catalyst.

11. The composition of claim 10, wherein the high temperature stable phase transfer catalyst is selected from the group consisting of an alkyl guanidinium salt, an aryl guanidinium salt, an alkyl phosphonium salt, an aryl phosphonium salt, a peralkylated phosphazenium salt, and any combination thereof.

12. A method of inhibiting corrosion, comprising:
adding a composition according to claim 1 to an industrial water system comprising a metallic surface.

13. A composition, comprising: a compound or salt thereof of formula (I), an acid, and sulfolane;

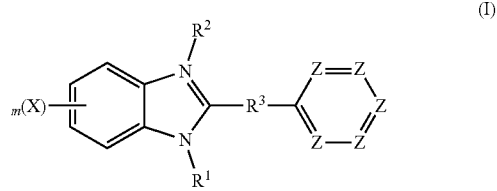

wherein
X is independently hydrogen, halogen, or a substituted or unsubstituted $C_{1-5}$ alkyl group, and m is 1, 2, 3, or 4;
$R^1$ is hydrogen, a substituted or unsubstituted $C_1$-$C_{12}$ alkyl group, or a substituted or unsubstituted $C_4$-$C_6$ aryl group;
$R^2$ is absent, hydrogen, a substituted or unsubstituted $C_1$-$C_{12}$ alkyl group, or a substituted or unsubstituted $C_4$-$C_6$ aryl group;
$R^3$ is a bond or $CHR^4$;
$R^4$ is hydrogen, halogen, $NR^5R^6$, or $OR^5$;
wherein $R^5$ and $R^6$ are each independently hydrogen, a substituted or unsubstituted $C_1$-$C_{12}$ alkyl group, or a substituted or unsubstituted $C_4$-$C_6$ aryl group; and
Z is independently nitrogen, CX, or $N^+R^5$.

* * * * *